(12) United States Patent
Maccioni et al.

(10) Patent No.: US 9,012,237 B2
(45) Date of Patent: Apr. 21, 2015

(54) INNOVATIVE BLOOD PLATELETS BIOMARKER FOR EARLY DIAGNOSIS OF ALZHEIMER'S DISEASE

(75) Inventors: Ricardo B. Maccioni, Santiago (CL); Gonzalo Farias, Santiago (CL)

(73) Assignee: Servicios Cientificos Neuroinnovation Limitada, Santiago (CL)

( * ) Notice: Subject to any disclaimer, the term of this patent is extended or adjusted under 35 U.S.C. 154(b) by 275 days.

(21) Appl. No.: 13/318,899

(22) PCT Filed: Nov. 5, 2010

(86) PCT No.: PCT/US2010/055623
§ 371 (c)(1),
(2), (4) Date: Nov. 4, 2011

(87) PCT Pub. No.: WO2011/062782
PCT Pub. Date: May 26, 2011

(65) Prior Publication Data
US 2012/0058573 A1 Mar. 8, 2012

Related U.S. Application Data

(60) Provisional application No. 61/281,442, filed on Nov. 17, 2009.

(51) Int. Cl.
*G01N 33/53* (2006.01)
*G01N 33/536* (2006.01)
*G01N 33/541* (2006.01)
*G01N 33/577* (2006.01)
*G01N 33/68* (2006.01)

(52) U.S. Cl.
CPC .... *G01N 33/6896* (2013.01); *G01N 2800/2821* (2013.01)

(58) Field of Classification Search
CPC .......... G01N 33/6896; G01N 2500/04; G01N 2800/2821; A61K 38/00; C07D 239/42
USPC .............................. 435/7.1; 422/430; 436/501
See application file for complete search history.

(56) References Cited

U.S. PATENT DOCUMENTS

| 6,670,137 B2 * | 12/2003 | VanMechelen et al. ........ 435/7.1 |
| 2001/0018191 A1 | 8/2001 | Mercken et al. |
| 2002/0086009 A1 | 7/2002 | Ishiguro et al. |
| 2003/0096227 A1 * | 5/2003 | Shinitzky et al. .................. 435/6 |
| 2007/0157325 A1 * | 7/2007 | Mojtahedian .................... 800/12 |

OTHER PUBLICATIONS

Borroni et al., Eur. J. Pharmacol., vol. 545, 2006, pp. 73-80.*
Li et al., Blood, vol. 111, Jan. 24, 2008, pp. 3522-3530.*
Berger et al., J. Neurosci., vol. 27, 2007, pp. 3650-3662.*
Goedert et al., Monoclonal antibody AT8 recognizes tau protein phosphorylated at both serine 202 and threonine 205, Neuroscience Letters, vol. 189, pp. 167-170, Apr. 21, 1995.
Ishiguro et al., Phosphorylated tau in human cerebrospinal fluid is a diagnostic marker for Alzheimer's disease, Neuroscience Letters, vol. 270, pp. 91-94, Jul. 30, 1990.
Thangavel et al., The abnormally phosphorylated tau lesion of early Alzheimer's disease, Newrochem Res., vol. 34, pp. 118-123, Jan. 2009.
Rosen et al., Relating medical temporal lobe volume to frontal fMRI activation for memory encoding in older adults, Stanford University, CA, USA, Cortex, 41, pp. 595-602, 2005.
Romeo et al., CSF proteome: a protein repository for potential biomarker identification, Expert Rev. Proteomics 2(1), pp. 57-70, www.future-drugs.com, 2005.
Verboeff et al., In-Vivo imaging of Alzheimer disease b-Amyloid with [11C]SB-13 PET, Am J Geriatr Psychiatry 12:6, pp. 584-595, Nov.-Dec. 2004.
Winblad et al., Pharmacotherapy of Alzheimer's disease: is there a need to redefine treatment success?, Int. J Geriatr Psychiatry, 16, pp. 653-666, 2001.
Neumann et al., Human platelet tau: A potential peripheral marker for Alzheimer's disease, Journal of Alzheimer's Disease 25, pp. 103-109, 2001.
Okamura et al., Quinoline and Benzimidazole Derivatives: candidate probes for in Vivo Imaging of Tau pathology in Alzheimer's disease, The Journal of Neuroscience—25(47), pp. 10857-10862, Nov. 23, 2005.
Mosconi et al., Reduced Hippocampal metabolism in MCI and AD, Automated FDG-PET image analysis, Neurology, vol. 64, pp. 1860-1867, 2005.
Godbolt et al., MRS shows abnormalities before symptoms in familial Alzheimer's disease, Neurology, vol. 66, pp. 718-722, 2006.
Chetelat et al., Early diagnosis of Alzheimer's disease: contribution of structural neuroimaging, www.sciencedirect.com., NeuroImage, vol. 18, pp. 525-541, 2003.
Moskoni et al., F-FDG Pet database of longitudinally confirmed healthy elderly individuals improves detection of mild cognitive impairment and Alzheimer's disease, J Nucl Med, vol. 48, pp. 1129-1134, 2007.
Mathis et al., Imaging technology for neurodegenerative diseases, Progress toward direction of specific pathologies, Arch Neurol, vol. 62, pp. 196-200, www.archneurol.com, Feb. 2005.

(Continued)

*Primary Examiner* — Jeffrey Stucker
*Assistant Examiner* — Stephen Gucker
(74) *Attorney, Agent, or Firm* — Gottlieb, Rackman & Reisman PC

(57) ABSTRACT

The present invention is directed to a method for early, non-invasive, rapid, efficient, reliable and accurate diagnose of Alzheimer's disease. The present invention particularly addresses obtaining blood samples, and stabilizing platelets from healthy persons and patients with probable cognitive impairment and/or Alzheimer's disease; extracting proteins from the platelets; identifying both monomeric and oligomeric tau proteins in the platelets with at least two monoclonal antibodies against the tau proteins, quantifying the amounts of the identified tau proteins, and comparing the amounts and protein profiles of the tau molecular species in the platelets of the healthy person and the patient.

12 Claims, 5 Drawing Sheets

(56) References Cited

OTHER PUBLICATIONS

Klunk et al., Imaging brain amyloid in Alzheimer's disease with Pittsburgh Compound-B, Ann Neurol, vol. 55, pp. 306-319, 2004.

Moskoni et al., Early detection of Alzheimer's disease using neuroimaging, Experimental Gerontology, vol. 42, pp. 129-138, www.sciencedirect.com, 2007.

Rusinek et al., Regional brain atrophy rate predicts future cognitive decline: 6 year Longitudinal MR imaging study of Normal Aging, Radiology, vol. 229, pp. 691-696, 2003.

Maccioni et al., The molecular bases of Alzheimer's disease and other neurodegenerative disorders, Archives of Medical Research, vol. 32, pp. 367-381, 2001.

Huhmer er al., Protein analysis in human cerebrospinal fluid: physiological aspects, current progress and future challenges, Disease Markers, vol. 22, pp. 3-26, 2006.

* cited by examiner

INNOVATIVE BLOOD PLATELETS BIOMARKER FOR EARLY DIAGNOSIS OF ALZHEIMER'S DISEASE

This application claims priority from U.S. provisional application 61/281,442, filed Nov. 17, 2009.

FIELD OF THE INVENTION

The present invention correponds to a highly innovative, efficient and non-invasive biomarker for early diganosis of Alzheimer's disease (AD). This molecular marker is based on the relationship between tau variants of low molecular weight (LMW-tau) and high molecular weight (HMW-tau) present in isolated and stabilized platelets from the blood of AD patients.

STATE OF THE ART

Neurodegenerative diseases and disorders, along with vascular disease and cancer are major public health problems. Because of the relevance and impact that have reached in the population, are among the leading causes of morbidity and death. Among the neurodegenerative disorder Alzheimer's disease (AD) is one of the most relevant, it corresponds to a brain disease that causes memory problems, also affecting the thinking and character, or how to behave. This disease is not a form of normal aging. It is one of the most common forms of dementia, a general term to describe loss of memory and other thinking skills, and its impact is so severe and complex, that it interferes with daily life of the individual.

AD is a health problem difficult to treat and it requires an early diagnosis to be controllable or to reduce its effects. AD has a major impact on the public health system and it is the most important cause of dementia, accounting for 50 to 70 percent of cases. It is the fourth leading cause of death in the world after cardiovascular disorders. The prevalence of AD in the world is 12% in those older than 65 years. The mortality rate is 100,000 people per year and the cost for the U.S. economy is USD 170 million annually (Wimo and Jonsson, 2001; Winblad et al, 2001). Dementia, a syndrome characterized by decline in cognitive functions and capabilities, affects a significant percentage of this population. Within the dementia, the AD is the highest prevalence and incidence. This means a great cost to the state, and it has been determined that there has been an increased incidence of AD due to the increase in life expectancy. Besides, there is a group of diseases related to AD, the tauopathies, in which tau protein, an essential component of the cytoskeleton, which is added in the brain to form structures called neurofibrillary tangles (NFTs) (Maccioni and Cambiazo, 1995a; Maccioni et al, 2001). The NFTs are formed by polymeric aggregations of tau, a protein that has been investigated in depth in the context of AD, for over 30 years (Maccioni, 1986; Maccioni et al, 1995b; Maccioni et al, 2001). These diseases have no cure to date, but finding an early diagnostic procedure for detection of the disease would substantially increase survival and quality of life of the patients. In addition, procedures and technologies that enable accurate diagnosis of AD will stimulate the development of therapies to bring the disease under control.

Historically, there have been two positions on the evaluation and indicators of neurodegenerative diseases and in particular of AD. One is the monitoring and identification of senile plaques and amyloid-beta peptide (Aβ), the other is the Tau protein and its alterations as neurofibrillary tangles (NFTS) and hyperphosphorylation process. Publications of Klunk et al. (Klunk et al, 2004), Verhoeff et al. (Verhoeff et al, 2004), Glodzik et al. (Glodzik-Sobanska et al, 2005) and Mosconi et al. (Mosconi et al, 2007a; Mosconi et al, 2005) has shed some light on markers of senile plaques, but despite having been developed several years ago, its clinical application has not been established or implemented. The development of radio-ligands for in vivo imaging of Aβ plaques and NFTS, either by PET, SPECT or other technologies, is now an important and active area of Nuclear Medicine. The design and biological evaluation of agents for imaging of Aβ plaques, either by PET or SPECT requires knowing the structure-function relationships of these radiotracers ranging from large proteins and peptides such as Aβ and radioactive monoclonal antibodies to small molecules derived from Congo red, Chrisamine-G, thioflavine-T, and acridine orange. Recent studies have shown that with this type of technology it is possible to obtain images in vivo in humans suggestive of both senile plaques and the NTFS, but this correlation has not been established. So far the most useful radiotracers have been relatively small molecules (<600 Da). The development of radiotracers for in vivo imaging of Aβ-amyloid plaques (PAB) and NFTS, either by PET or SPECT, has been an important and active area of radiopharmaceutical industry (Mathis et al, 2005).

Until now, different types of neuroimaging techniques have been used without success as an approach to diagnosis and evaluation of the evolution of AD and tauopathies (Godbolt et al, 2006; Mathis et al, 2005; Rosen et al, 2005; Rusinek et al, 2003; Stoub et al, 2005). In summary, the standard diagnostic procedures by neuroimaging are not specific for AD, since virtually all efforts to achieve a neuroimaging technology for AD have focused on the deposits of amyloid, including the "Pittsburgh compound" (GDP) and 2-(1-(6-[(2-[F-18]fluoroethyl) (methyl)amino]-2-Naphthyl)ethylidene) Malononitrile (FDDNP) (Boxer et al, 2007; Klunk et al, 2004; Mosconi et al, 2007b), which recognize both the amyloid and the NFTS and does not allow a selective display. In addition, the implementation of diagnostic neuroimaging is a process that can result to high costs, it needs sophisticated equipments and it results are somewhat specific. It should be noted that the confirmatory diagnosis of AD can only be done by neuropathology, after "postmortem" analysis of brain tissue. There are some approaches to address the need for early diagnosis (Okamura, 2004; Okamura et al, 2005), but these have not been entirely satisfactory or specific, and the cannot solve the problem of AD early diagnosis (US2006018825, WO02069965).

Therefore an early, specific pathological diagnosis that enables a presymptomatic diagnosis of AD is required; that would allow us understand the natural progression of the disease and its pathophysiology.

A first approximation to such a solution is through the evaluation of cerebrospinal fluid. This fluid is in equilibrium with the brain, spine and extra cellular fluid, thus the fluid is a reservoir which reflects the health status and activity of the central nervous system. Thus Huhmer et at (2006) and Romeo et al, (2005) describes a set of proteins in cerebrospinal fluid have been studied as potential markers of neurological diseases.

This has also been proposed in U.S. Pat. No. 5,262,332 that one can develop a method for diagnosing Alzheimer's disease based on the detection of Aβ protein, its precursor or a fragment of the same in biopsies of non neural tissue using immunoassay techniques. However, this approach is not specific. It has been recognized that a wide variety of degenerative diseases induces the deposition of Aβ protein in nearly all human tissues. Therefore, since the Aβ protein is deposited in many tissues of patients with Alzheimer's disease, this definitely should not be linked to Alzheimer's in a different way to their association with many other degenerative diseases. Therefore, the diagnostic utility of antibodies directed to Aβ protein, their precursors or any of its fragments must be considered marginal at best.

Furthermore, it is known that in Alzheimer's disease neurofibrillary tangles are generated Tau protein which presents a hyperphosphorylation. Considering this, the patent application US2002086009 (WO9734145) describes obtaining an antibody to an epitope of phosphorylated Tau protein, where the antibody is used to identify the immunogenic target in different samples and biopsies of tissue from the brain or organic fluids such as cerebrospinal fluid or blood. (note that this technique allows to identify the tau protein in brain samples and biopsies, and is not a tool for early NON INVASIVE diagnosis).

Also in the Japanese patent application JP 2002040023 the identification of Tau protein in blood samples from patients who have the possibility of getting AD is described (notably, evaluation is done in plasma, not in blood cells).

SUMMARY OF THE INVENTION

Figure 1:
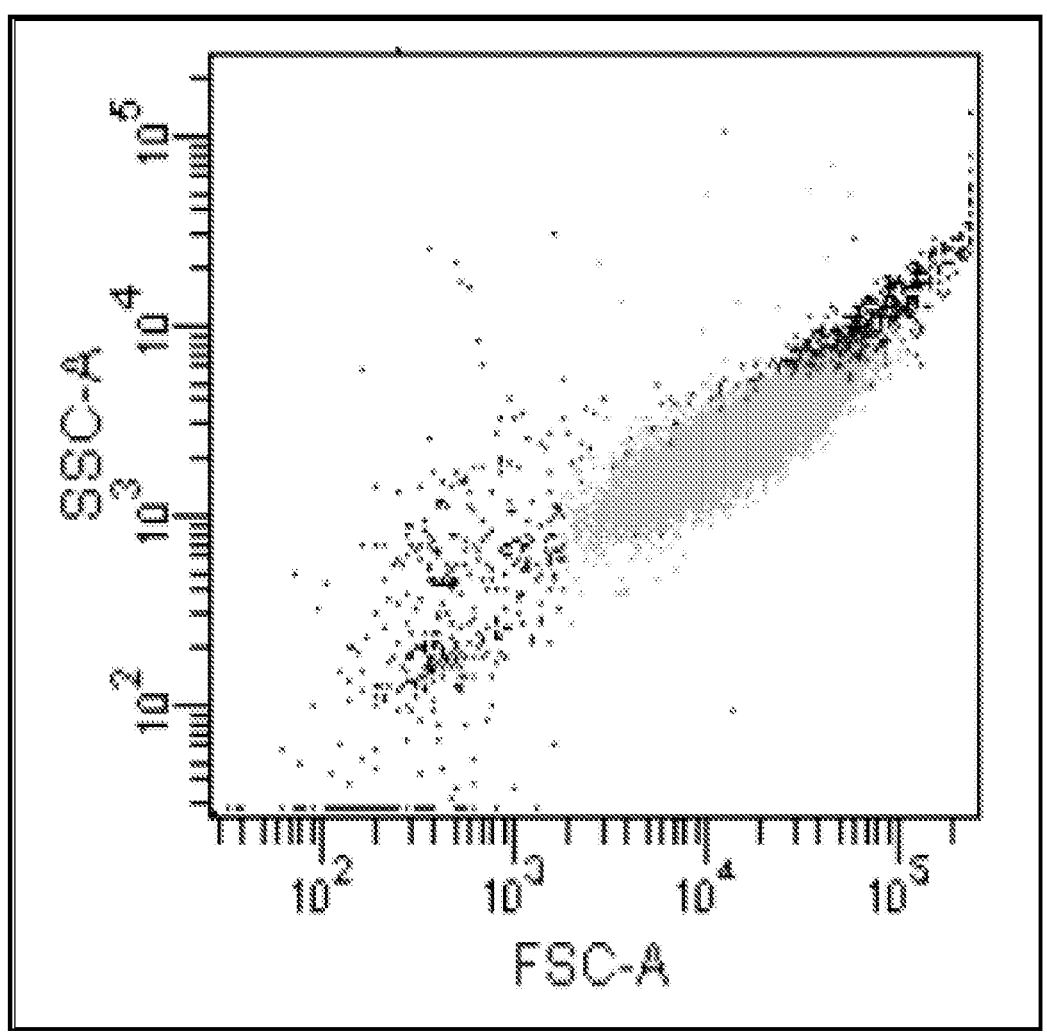
FIG. 1: Characteristic light-scatter profile of a platelet isolated from whole blood and fixed. Data are collected and displayed using logarithmic-orthogonal and logarithmic-forward light scatter. Single platelet events are identified by their characteristic light-scatter properties. In green, singles platelets count (84.1%); in red all platelets—singles and aggregated (89.8%).

The present invention relates to a method of detection and monitoring of a highly efficient biomarker in biological samples from patients with neurodegenerative diseases or tau pathologies. Furthermore the invention relates to a kit comprising monoclonal antibodies, polyclonal or fragments of them for the diagnosis of those pathologies. This new technology is highly specific and reliable for the diagnosis of Alzheimer's disease or other types of neurodegenerative diseases or tau pathologies. Particularly it focuses on identifying patterns of altered tau proteins.

DETAILED DESCRIPTION OF THE INVENTION

The present invention comprises a method and a kit intended for early, non-invasive, rapid, efficient, reliable and accurate diagnostic determination of a biomarker in biological samples from patients suspected susceptible or afflicted with neurodegenerative diseases or Tau disorders, preferably AD. The proposed method and kit identifies a biomarker that corresponds to altered Tau protein, preferably a heavy variant of the Tau protein, which has a molecular weight of approximately 140 kDa present in biological samples. This protein is found in biological fluids, preferably blood. In one form the invention comprises a method and a kit allowing the detection of heavy variant of the Tau protein with a molecular weight of approximately 140 kDa in platelets. The method of the invention comprises the identification of Tau proteins in platelets with at least two monoclonal antibodies to Tau, where at least one of them is directed to hyperphosphorylated variants of Tau protein.

The method of diagnosis includes obtaining and stabilizing platelets, extracting the proteins, then the analysis of platelet proteins electrophoresis pattern in 1-D and 2-D gels and immunoassay. Preferred immunoassay is performed with antibodies against different variants of tau (total tau, hyperphosphorylated tau or heavy type tau), for example Tau5 antibodies, AT8 and PHF1.

The proposed diagnostic method involves collection of blood samples in tubes with anticoagulants regularly used in the state of the art, preferably K2EDTA separating the platelets by differential centrifugation, stabilization of platelets and the extraction of proteins in the presence of proteinase inhibitors, preferably by the addition of cold RIPA and a mixture of proteinase inhibitors, then centrifugation at 1500 g for at least 10 minutes at 4° C. The concentration of proteins will be determined by the method of Bradford. Optionally, the sample can be frozen in tubes at about −80° C. without preservatives.

The proteins are separated by SDS-PAGE polyacrylamide gels in 10% gels and then bi-dimensional (2D) to separate the variants of Tau. Proteins are transferred to a nitrocellulose membrane and analyzed by immunodetection (Western Blot) with an antibody that recognizes total Tau (Tau5) and AT8 and PHF1 antibodies for hyperphosphorylated Tau variants. Then, a registration method, preferably chemiluminescence with a horseradish (HRP) conjugated antibody against the first antibody is used.

Example for the Method
Patient Selection

Five different groups of subjects older than 61 years were recruited, which showed the following characteristics: 1) mild Alzheimer; 2) moderate Alzheimer; 3) advanced Alzheimer, 4) Mild cognitive impairment (MCI) and 5) control subjects. The subjects underwent a multi-stage procedure, with criteria including i) aged 65-75 years, ii) patients with Alzheimer's disease must comply NINCDS-ADRDA criteria (Dubois et al, 2007) and the MCI group agreed with the approach of Peterson (Maccioni et al, 2006), iii) be free of medical illnesses, neurological or psychiatric that may affect participation in the study or treatment outcome, and iv) be willing to participate after informed consent procedure of the study. The evaluation included brain imaging using computerized axial tomography or MRI, to exclude vascular lesions of the brain, neoplasms, subdural hematomas and other conditions that could explain the dementia or interfere with the study.

At the time of recruitment, patients were grouped by gender, educational level and demographic aspects. The control subjects were selected with a distribution of gender and similar age. The subjects of the study were from a region where 41% are Amerindian ancestry and 59% of Caucasian ancestry (Santiago, Chile).

Determination of Sample Size

The sample size (N) was determined using the program G*Power 3.0.10 (Franz Faul, Universität Kiel, Germany, http://www.psycho.uni-duesseldorf.de/abteilungen/aap/gpower3/) with an f=0.25 (Cohen, 1988), a power of 0.95 and a significance of 0.05. We calculated a sample size of 305 subjects, with 61 subjects per group.

Set of Neuropsychological Tests.

The subjects in the study underwent a neuropsychological assessment. The neuropsychological evaluation consisted in the examination of Folstein and colleagues minimental State (MMSE), Neuropsychiatric Inventory (NPI) and Alzheimer's disease Assessment Scale (ADAS-Cog). Statistical comparisons of age, education and cognitive measures were performed using one-way analysis of variance (ANOVA) with each measure as the dependent variable comparing the groups. Comparisons of pair-wise between adjacent groups were made by Tukey's Honestly Significant Difference at a significance level set at 0.05.

Sampling

Blood samples (5 ml per patient) were obtained by venous puncture early in the morning after 8-10 hours of fasting. Platelets were immediately separated. A portion of each sample was preserved in polypropylene tubes without preservative, frozen in dry ice and stored at −80° C.

Preparation of Samples for Platelets Proteomics.

Platelets separated from fresh blood samples under conditions to prevent their activation. Venous blood was extracted into EDTA tubes (BD Vacutainer K2E, 10.8 mg) and kept at room temperature for processing during the day.

Platelets were separated by differential centrifugation according to Rao (1988) with modifications involving spin at room temperature. The first centrifugation was run at 200 g for 10 minutes to obtain platelet-rich plasma, which is then centrifuged at 200 g for 10 minutes to remove the contamination of red blood cells and lymphocytes. The third stage centrifugation runs at 1600 g for 10 minutes to obtain a platelet pellet. Platelet poor plasma was removed and platelet pellet was carefully resuspended in 0.83% NH4Cl at room temperature to lyse red blood cells remaining. The following centrifugation is performed at 1500 g for 10 minutes and supernatant was extracted. The platelet pellet was washed twice with phosphate buffer solution (PBS) and again centrifuged at 1500 g for 10 minutes. The purity of separated platelets was determined by Romanowsky staining Platelets were kept on ice to prevent proteolysis.

Platelet proteins were extracted by the addition of cold RIPA and a mixture of proteinase inhibitors, then centrifuged at 1500×g for 10 minutes at 4° C. The concentration of protein is determined by the method of Bradford.

Electrophoresis.

Electrophoresis was run at 1 and 2 dimensions. It ran a denaturant polyacrylamide gel (SDS-PAGE) according to the method of Laemmli (Laemmli, 1970). A total of 100 mg of platelets protein was charged per well on 10% acrylamide gels.

The gel electrophoresis was performed for 2-dimensional analysis of Tau variants according to O'Farrell (1975). A total of 200 mg of platelet protein was loaded per gel. Strips of immobilized pH gradients BioRad (pH 3-10) was used for separation of proteins in the first dimension and 10% SDS-PAGE was performed for the second dimension.

Immunoblot.

Figure 2:
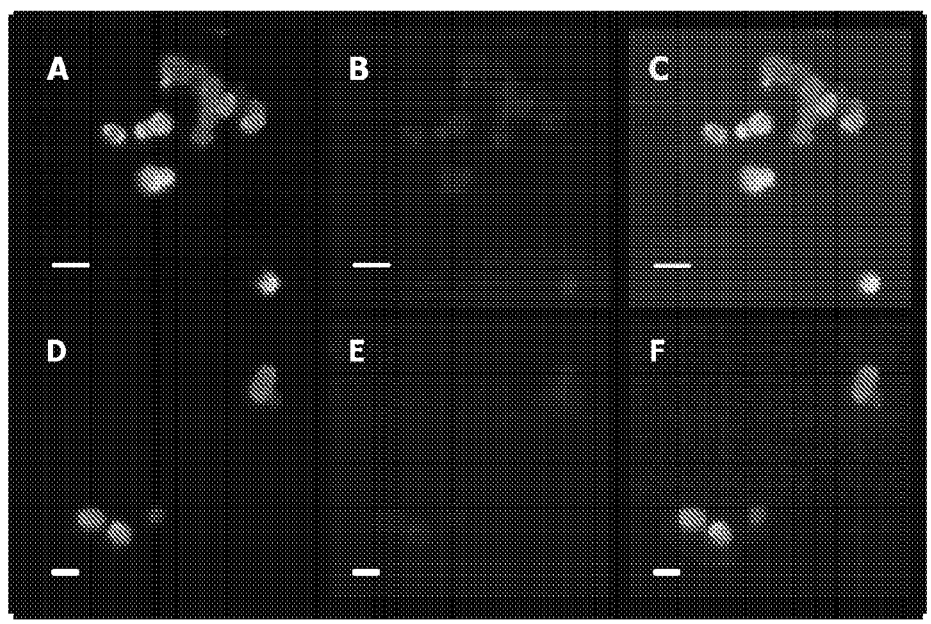
FIG. 2: fluorescence microscopy of platelets isolated from control subjects (A-C) and AD patients (D-F). A and D: F-actin (alexa conjugated phalloidin); B and E: tau immunofluorescence (tau-5 antibody); C and F; merge. Bar represents 10 μm.
Figure 3:
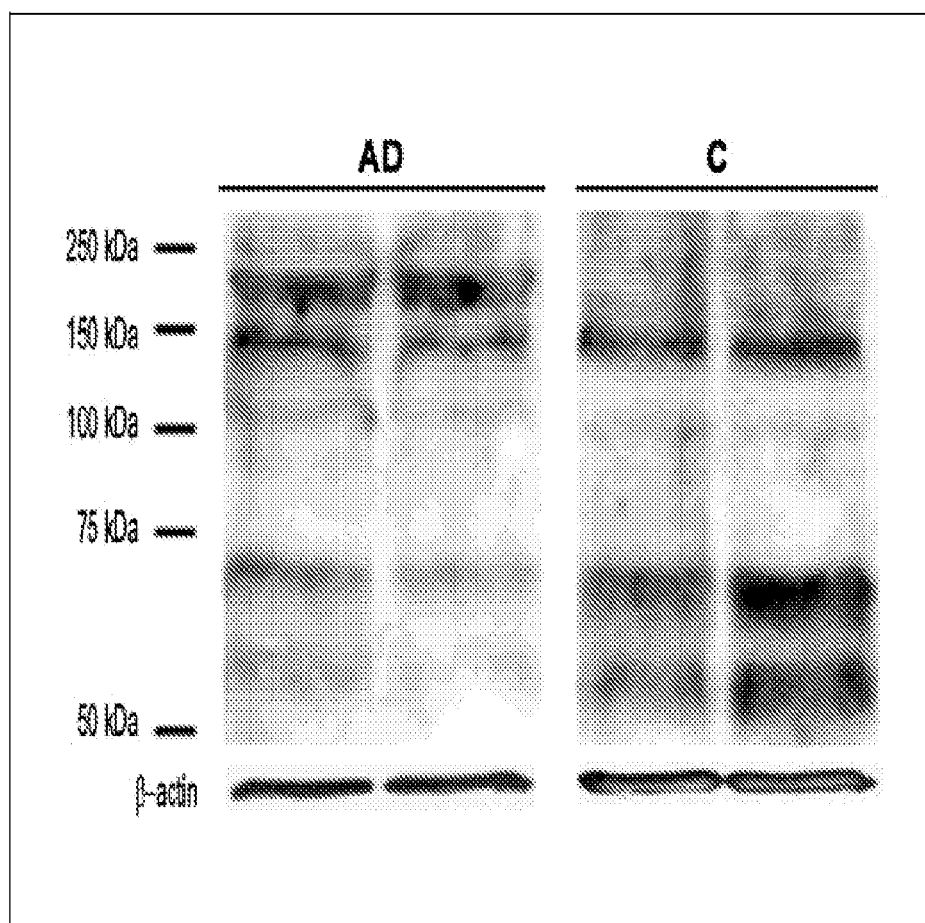
FIG. 3: Immunoblot of total platelets protein detecting tau variant by Tau5 immunoreactivity. Representative HMW-tau bands are over the 140 kDa and LMW-tau bands are under 75 kDa of two AD subjects (AD) and two normal subjects (C). β-actin as load control in the inferior part.
Figure 4:
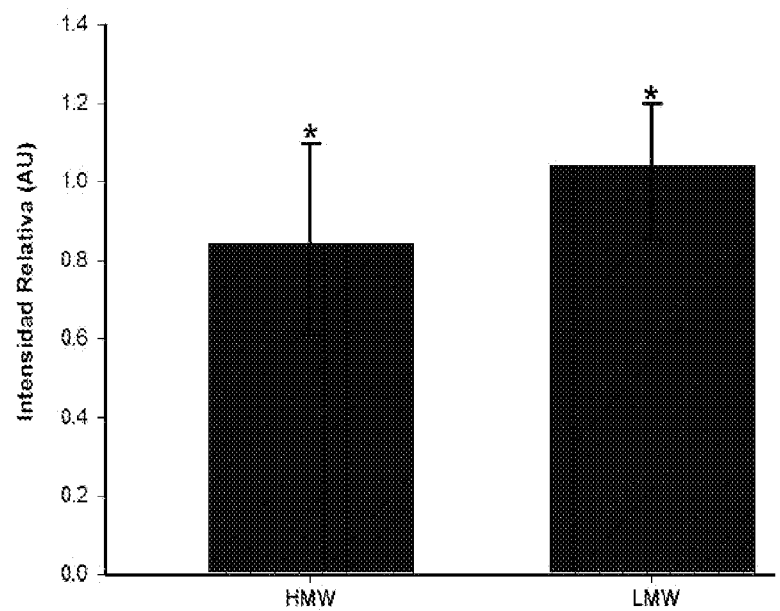
FIG. 4 shows the relative amount of Tau variants of high molecular weight (HMW) and LMW in platelets obtained from normal subjects. Which is quantified by densitometry of Tau variants, identified by immunoreactivity to Tau 5 antibody. HMW: High Molecular Weight, LMW: low molecular weight. n=8. Mean±SD. T Test: *p<0.01.
Figure 5:
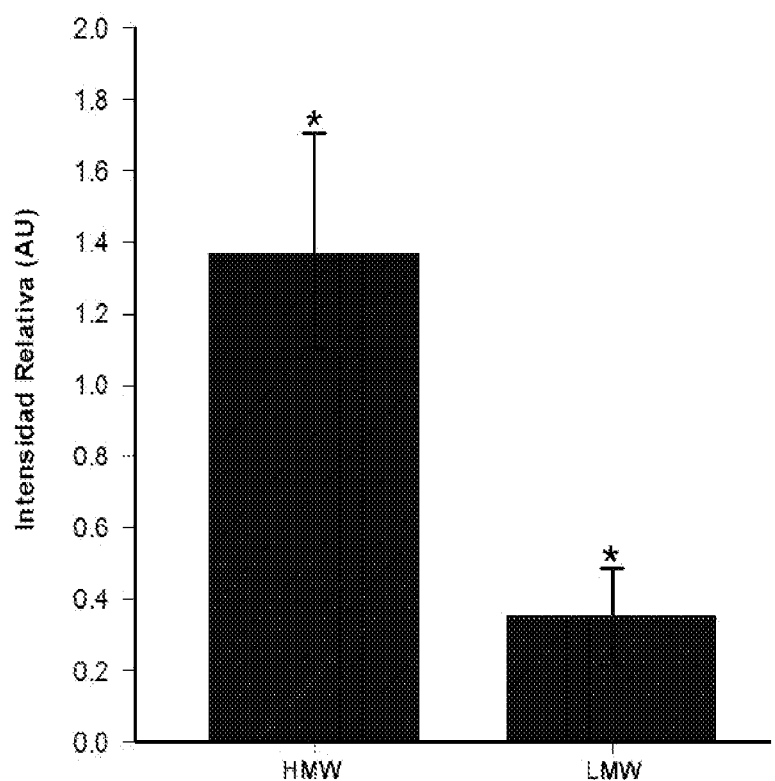
FIG. 5 shows the relative amount of HMW and LMW Tau variants in platelets of subjects with Alzheimer's disease. Quantification is made by densitometry of Tau variants, identified by immunoreactivity to Tau 5 antibody. HMW: High Molecular Weight, LMW: low molecular weight. n=5. Mean±SD. T Test: p<0.01.

The proteins separated in 1D and 2D gels were transferred to nitrocellulose membranes. Each membrane was blocked with 5% non fat dry milk. The immobilized proteins were tested with specific antibodies against tau protein such as Tau5 to identify tau variants, AT8 and PHF1 to identify hyperphosphorylated Tau variants and anti human β-actin as protein load control. All antibodies were tested in the same membrane, one by one, followed by membrane antibody stripping and re-test. An HRP conjugated antibody was used as second antibody. The visualization of antigens was performed by chemiluminescence using a kit of reagents for ECL Western blotting detection (Amersham) according to manufacturer's instructions. The luminescence was recorded on film detection TCL. The protein bands of the film were scanned and digitized to quantify the intensity using the program Image 1.40 (NIH). The intensity of the band of protein of interest was divided by the intensity of the band that represents the control (β-actin) to calculate the relative amount (Maccioni et al, 2006). The results were plotted and the difference between normal subjects and Alzheimer patients is shown in FIGS. 1 and 2. It is appreciated that in healthy persons there is no difference in the profile of tau at high or low molecular weight, whereas in Alzheimer's patients the difference is significant and clear.

Example of the Platelet Biomarker Kit for Early Diagnosis of Alzheimer's Disease Considering that we have developed the technology to generate a non-invasive blood biomarker tool for early diagnosis of Alzheimer's disease by analysis of tau protein variants in the platelets, using immunoblot techniques and densitometric analysis, we propose to carry out the packaging of the materials needed for this type of analysis, along with detailed instructions for performing all the steps required. This will be introduced in the form of a kit based on the technology of this patent document, intended for use in clinical laboratory.

The proposed kit corresponds to a group of materials and solutions, which in turn are divided into separate, properly identified sets of supplies corresponding to the elements needed to perform each sequential step required for the described technology, which can be detailed as follows:

A) Collection and processing of peripheral venous blood samples for platelet isolation and extraction of total platelet proteins B) Electrophoresis of total proteins in acrylamide/bisacrylamide gels and transfer to nitrocellulose membranes C) Immunoblots with specific antibodies against tau protein D) Scanning and densitometric analysis of platelets tau Below is a sample of the instructions provided and the steps necessary for implementing the kit.

1) Initial Processing of Venous Blood Samples.

A 5 cc sample of venous blood is obtained in a tube with K2EDTA (BD Vacutainer™) The sample stored at room temperature should be processed as soon as possible (within one hour for best results). The sample is centrifuged in a clinical centrifuge at 200 g for 10 minutes at room temperature and a supernatant platelet-rich plasma (PRP) is obtained. The rest of the sample is discarded and the PRP is centrifuged at 1600 g for 10 minutes to obtain a platelets pellet. 150 μL of radio-immunoprecipitation buffer (RIPA) and 3 μL of protease inhibitor cocktail are added and the pellet is resuspended. The mix is centrifuged at 1500 g for 10 minutes and the pellet is discarded. The samples (supernatant) can be stored at −20° C. until further analysis.

2) Polyacrylamide Gel Electrophoresis

Platelets total protein separation is performed in a minigel according to the technique of Laemmli (Laemmli, 1970). 50 mcg of the sample protein are loaded in a 10% polyacrylamide-bisacrylamide gel and electrophoresis is performed under denaturing conditions (SDS-PAGE) at 100 mV for 90 minutes.

3) Immunoblot

The sample is transferred to a nitrocellulose membrane in a tank for an hour at 100 mV.

The membranes are blocked with 3% bovine serum albumin (BSA) and then incubated with the antibody tau 5 (2 µg/ml), and with a secondary HRP-conjugated anti mouse antibody to recognize the tau protein variants. A chemiluminescence reaction is carried out with SuperSignal West Femto Maximum Sensitivity Substrate (Thermo Scientific).

4) Densitometric Analysis.

The signal is detected on photographic plate, digitized in a scanner and the intensities of the bands are analyzed with ImageJ 1.40 software (National Institutes of Health, USA). The ratio between tau forms of high molecular weight>70 kDa and forms of <70 kDa is evaluated (this ratio is increased in patients with Alzheimer's Disease).

The kit is intended for the analysis of 18 samples and includes:
25 Vacutainer™ EDTA tubes
2 ml Eppendorf tubes for Molecular Biology Neptune™ Plastics (80 tubes)
A bottle with 10 ml 10× red blood cells lysis buffer (1.5 M $NH_4Cl$, 100 mM $NaHCO_3$, 10 mM $Na_2EDTA$).
10 ml RIPA solution (5.0 mM Tris-HCl pH 7.5, 1.5 mM NaCl, 10% NP-40, 10% deoxycholate, 20 mM EDTA pH 8.0, 500 mM NaF, 1% SDS)
60 ul protease inhibitors cocktail (sigma)
Two 10% acrylamide/bisacrylamide gels (0.015% SDS)
1 ml 5× loading buffer (60 mM Tris-HCl pH 6.8, 25% glycerol, 14.4 mM 2-mercapto ethanol, 0.1% bromophenol blue, 2% SDS)
2 Eppendorf tubes with 10 µl of molecular weight marker 10 to 250 KDa (PageRuler™ Plus prestained protein ladder from Fermentas)
1 package to reconstitute 2 liters of run buffer (0.39 M glycine, 1.18 M Tris Base)
SDS (2 ml) to reconstitute 20 ml of 10% SDS
Technical grade methanol (200 ml)
A package to reconstitute 2 liters of phosphate buffered saline (PBS) (270 mM NaCl, 5.37 mM KCl, 10.14 mM $Na_2HPO_4$, 1.76 mM $KH_2PO_4$)
2 nitrocellulose membranes of 8×6 cm, (Amersham Biosciences Hybond™-C)
Package with 0.5 ml of Tween 20 to reconstitute 1 liter of PBS-Tween0.05%
A bottle containing 100 ml of 3% BSA in PBS (blocking solution)
A bottle containing 50 ml of 2 ug/ml tau 5 antibody and 1% BSA in PBS (antibody solution 1)
A bottle containing 100 ml of HRP-conjugated anti Mouse antibody 0.05 ug/ml (Santacruz Biotechnology) and 1% BSA in PBS (antibody solution 2)
Chemiluminescense kit SuperSignal West Femto Maximum sensitivity Substrate™ (Thermo Scientific) divided in two bottles of 10 ml each Equipment needed but not supplied with the kit
Container for running acrylamide gels (eg BioRad mini protean III™)
Power source capable of generating at least 100 mV
Equipment for transfer from gels to nitrocellulose membranes
Photographic films
Solutions for developing and fixing photographic films
Digitizing equipment (scanner or digital camera)
Software for densitometric analysis (eg ImageJ http://rsbweb.nih.gov/ij/index.html)

References

Boxer A L, Rabinovici G D, Kepe V, Goldman J, Furst A J, Huang S C, Baker S L, O'Neil J P, Chui H, Geschwind M D, Small G W, Barrio J R, Jagust W, Miller B L (2007) Amyloid imaging in distinguishing atypical prion disease from Alzheimer disease. *Neurology* 69: 283-290.

Cohen J (1988) Statistical Power Analysis for the Behavioral Sciences. Lawrence Erlbaum Associates, Hillsdale, N.J.

Dubois B, Feldman H H, Jacova C, Dekosky S T, Barberger-Gateau P, Cummings J, Delacourte A, Galasko D, Gauthier S, Jicha G, Meguro K, O'Brien J, Pasquier F, Robert P, Rossor M, Salloway S, Stern Y, Visser P J, Scheltens P (2007) Research criteria for the diagnosis of Alzheimer's disease: revising the NINCDS-ADRDA criteria. *Lancet Neurol* 6: 734-746.

Glodzik-Sobanska L, Rusinek H, Mosconi L, Li Y, Zhan J, de Santi S, Convit A, Rich K, Brys M, de Leon M J (2005) The role of quantitative structural imaging in the early diagnosis of Alzheimer's disease. *Neuroimaging Clin N Am* 15: 803-826, x.

Godbolt A K, Waldman A D, MacManus D G, Schott J M, Frost C, Cipolotti L, Fox N C, Rossor M N (2006) MRS shows abnormalities before symptoms in familial Alzheimer disease. *Neurology* 66: 718-722.

Huhmer A F, Biringer R G, Amato H, Fonteh A N, Harrington M G (2006) Protein analysis in human cerebrospinal fluid: Physiological aspects, current progress and future challenges. *Dis Markers* 22: 3-26.

Klunk W E, Engler H, Nordberg A, Wang Y, Blomqvist G, Holt D P, Bergstrom M, Savitcheva I, Huang G F, Estrada S, Ausen B, Debnath M L, Barletta J, Price J C, Sandell J, Lopresti B J, Wall A, Koivisto P, Antoni G, Mathis C A, Langstrom B (2004) Imaging brain amyloid in Alzheimer's disease with Pittsburgh Compound-B. *Ann Neurol* 55: 306-319.

Laemmli U K (1970) Cleavage of structural proteins during the assembly of the head of bacteriophage T4. *Nature* 227: 680-685.

Maccioni R B (1986) Molecular cytology of microtubules. *Revis Biol Celular* 8: 1-124.

Maccioni R B, Cambiazo V (1995a) Role of microtubule-associated proteins in the control of microtubule assembly. *Physiol Rev* 75: 835-864.

Maccioni R B, Lavados M, Guillon M, Mujica C, Bosch R, Farias G, Fuentes P (2006) Anomalously phosphorylated tau and Abeta fragments in the CSF correlates with cognitive impairment in MCI subjects. *Neurobiol Aging* 27: 237-244.

Maccioni R B, Munoz J P, Barbeito L (2001) The molecular bases of Alzheimer's disease and other neurodegenerative disorders. *Arch Med Res* 32: 367-381.

Maccioni R B, Tapia L, Cambiazo V (1995b) Functional organization of tau proteins during neuronal differentiation and development. *Braz J Med Biol Res* 28: 827-841.

Mathis C A, Klunk W E, Price J C, DeKosky S T (2005) Imaging technology for neurodegenerative diseases: progress toward detection of specific pathologies. *Arch Neurol* 62: 196-200.

Mosconi L, Brys M, Glodzik-Sobanska L, De Santi S, Rusinek H, de Leon M J (2007a) Early detection of Alzheimer's disease using neuroimaging. *Exp Gerontol* 42: 129-138.

Mosconi L, Tsui W H, De Santi S, Li J, Rusinek H, Convit A, Li Y, Boppana M, de Leon M J (2005) Reduced hippocampal metabolism in MCI and AD: automated FDG-PET image analysis. *Neurology* 64: 1860-1867.

Mosconi L, Tsui W H, Pupi A, De Santi S, Drzezga A, Minoshima S, de Leon M J (2007b) (18)F-FDG PET database of longitudinally confirmed healthy elderly individuals improves detection of mild cognitive impairment and Alzheimer's disease. *J Nucl Med* 48: 1129-1134.

O'Farrell P H (1975) High resolution two-dimensional electrophoresis of proteins. *J Biol Chem* 250: 4007-4021.

Okamura N (2004) [In vivo imaging of amyloid plaques in the brain]. *Nippon Ronen Igakkai Zasshi* 41: 175-178.

Okamura N, Suemoto T, Furumoto S, Suzuki M, Shimadzu H, Akatsu H, Yamamoto T, Fujiwara H, Nemoto M, Maruyama M, Arai H, Yanai K, Sawada T, Kudo Y (2005) Quinoline and benzimidazole derivatives: candidate probes for in vivo imaging of tau pathology in Alzheimer's disease. *J Neurosci* 25: 10857-10862.

Rao G H (1988) Measurement of ionized calcium in normal human blood platelets. *Anal Biochem* 169: 400-404.

Romeo M J, Espina V, Lowenthal M, Espina B H, Petricoin E F, 3rd, Liotta L A (2005) CSF proteome: a protein repository for potential biomarker identification. *Expert Rev Proteomics* 2: 57-70.

Rosen A C, Gabrieli J D, Stoub T, Prull M W, O'Hara R, Yesavage J, deToledo-Morrell L (2005) Relating medial temporal lobe volume to frontal fMRI activation for memory encoding in older adults. *Cortex* 41: 595-602.

Rusinek H, De Santi S, Frid D, Tsui W H, Tarshish C Y, Convit A, de Leon M J (2003) Regional brain atrophy rate predicts future cognitive decline: 6-year longitudinal MR imaging study of normal aging. *Radiology* 229: 691-696.

Stoub T R, Bulgakova M, Leurgans S, Bennett D A, Fleischman D, Turner D A, deToledo-Morrell L (2005) MRI predictors of risk of incident Alzheimer disease: a longitudinal study. *Neurology* 64: 1520-1524.

Verhoeff N P, Wilson A A, Takeshita S, Trop L, Hussey D, Singh K, Kung H F, Kung M P, Houle S (2004) In-vivo imaging of Alzheimer disease beta-amyloid with [11C] SB-13 PET. *Am J Geriatr Psychiatry* 12: 584-595.

Wimo A, Jonsson L (2001) [Can the costs of future needs of health and social services for the elderly be calculated?]. *Lakartidningen* 98: 4042-4048.

Winblad B, Brodaty H, Gauthier S, Morris J C, Orgogozo J M, Rockwood K, Schneider L, Takeda M, Tariot P, Wilkinson D (2001) Pharmacotherapy of Alzheimer's disease: is there a need to redefine treatment success? *Int J Geriatr Psychiatry* 16: 653-666.

What is claimed is:

1. A method for determining an increased likelihood of Alzheimer's disease in a patient, said method comprising the steps of:
   characterizing quantities of high and low molecular weight Tau protein variants in a reference population of persons not suffering from Alzheimer's disease;
   obtaining and stabilizing platelets from a patient;
   extracting Tau protein variants from said platelets;
   using said extracted Tau protein variants, analyzing platelet proteins electrophoresis pattern in 1-D and 2-D gels;
   performing immunoassay with Tau5 anti-Tau antibodies directed against total Tau and using at least one antibody directed against hyperphosphorylated Tau selected from the group consisting of AT8 and PHF1 anti-Tau antibodies, thereby identifying Tau protein variants;
   comparing the relative amounts of high and low molecular weight Tau protein variants in the platelets of said patient to that of said reference population and determining an increased likelihood of Alzheimer's disease in a patient when the ratio of high to low molecular weight Tau protein variants in the immunoassay results exceeds said ratio in the reference population;
   wherein low molecular weight Tau protein variants are those of weight less than 70 kDa and high molecular weight Tau protein variants are those of weight greater than 70 kDa.

2. The method of claim 1, wherein high molecular weight Tau protein variants are limited to those of weight 140 kDa or greater.

3. The method of claim 1, wherein the step of performing immunoassay directed against hyperphosphorylated Tau is by using both AT8 and PHF1 anti-Tau antibodies.

4. The method of claim 3, wherein high molecular weight variants are limited to those of weight 140 kDa or greater.

5. A method for determining a likelihood of Alzheimer's disease in a patient, said method comprising the steps of:
   obtaining and stabilizing platelets from a patient;
   extracting Tau protein variants from said platelets;
   analyzing platelet proteins electrophoresis pattern in 1-D and 2-D gels and immunoassay;
   using antibodies, identifying Tau protein variants in platelets which h include at least two monoclonal antibodies directed against Tau, where at least one of them is directed against hyperphosphorylated variants of Tau protein, and characterizing these variants as low or high molecular weight Tau protein variants; and
   determining a likelihood of Alzheimer's disease in said patient when the ratio of high to low molecular weight Tau protein variants exceeds 1;
   wherein low molecular weight Tau protein variants are those of 70 kDa or less, high molecular weight Tau protein variants are those greater than 70 kDa, and said antibodies are Tau5 anti-Tau antibodies and at least one from the group consisting of AT8 and PHF1 anti-Tau antibodies.

6. The method of claim 5, wherein high molecular weight Tau protein variants are limited to those of weight 140 kDa or greater.

7. The method of claim 5, wherein the step of using antibodies is by using both AT8 and PHF1 anti-Tau antibodies.

8. The method of claim 7, wherein high molecular weight variants are limited to those of weight 140 kDa or greater.

9. A method for determining an increased likelihood of Alzheimer's disease in a patient, said method comprising the steps of:
   obtaining and stabilizing platelets from a patient;
   extracting Tau protein variants from said platelets;
   analyzing platelet proteins electrophoresis pattern in 1-D and 2-D gels and immunoassay thereby identifying Tau protein variants and determining their molecular weight;
   characterizing Tau protein variants in platelets which includes using at least two monoclonal antibodies to Tau; where at least one monoclonal antibody is directed to hyperphosphorylated variants of Tau protein which are high molecular weight variants if greater than 70 kDa, and characterizing Tau protein variants with molecular weight at 70 kDa or below as low molecular weight variants;
   separately quantifying the amounts of the extracted Tau protein variants by high and low molecular weight by densitometry of Tau protein variants, wherein the low molecular weight variants are identified by immunoreactivity to Tau5 anti-Tau antibodies and the high molecular weight Tau protein variants are identified by immunoreactivity to at least one anti-Tau antibody selected from the group consisting of AT8 anti-Tau antibodies and PHF1 anti-Tau antibodies; and determining an increased likelihood of Alzheimer's disease in a patient when the ratio of high to low molecular weight Tau protein variants exceeds 1.

10. The method of claim 9, wherein high molecular weight Tau protein variants are limited to those of weight 140 kDa or greater.

11. The method of claim 9, wherein the step of identifying by immunoreactivity is by using both AT8 and PHF1 anti-Tau antibodies.

12. The method of claim 11, wherein high molecular weight variants are limited to those of weight 140 kDa or greater.

* * * * *